(12) United States Patent
Nojiri et al.

(10) Patent No.: US 10,403,008 B2
(45) Date of Patent: Sep. 3, 2019

(54) IMAGE GENERATING APPARATUS AND CONTROL METHOD THEREFOR

(71) Applicant: CANON KABUSHIKI KAISHA, Tokyo (JP)

(72) Inventors: Yusuke Nojiri, Tokyo (JP); Nobu Miyazawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/807,743

(22) Filed: Nov. 9, 2017

(65) Prior Publication Data

US 2018/0144512 A1 May 24, 2018

(30) Foreign Application Priority Data

Nov. 21, 2016 (JP) .................. 2016-226067

(51) Int. Cl.
| | |
|---|---|
| *A61B 5/00* | (2006.01) |
| *G06F 3/0484* | (2013.01) |
| *G16H 30/20* | (2018.01) |
| *G06T 11/00* | (2006.01) |
| *G16H 10/60* | (2018.01) |
| *G06F 19/00* | (2018.01) |

(Continued)

(52) U.S. Cl.
CPC .......... *G06T 11/005* (2013.01); *A61B 5/0095* (2013.01); *G06F 3/04847* (2013.01); *G06F 19/321* (2013.01); *G06T 11/003* (2013.01); *G16H 10/60* (2018.01); *G16H 30/20* (2018.01); *G16H 40/63* (2018.01); *A61B 5/14532* (2013.01); *A61B 5/14542* (2013.01); *A61B 5/4312* (2013.01); *G06T 2200/24* (2013.01); *G06T 2211/40* (2013.01)

(58) Field of Classification Search
CPC . G06T 11/005; G06T 11/003; G06T 2200/24; G06T 2211/40; G06F 19/321; G06F 3/04847; G16H 10/60; G16H 40/63; G16H 30/20; A61B 5/0095; A61B 5/4312; A61B 5/14542; A61B 5/14532
See application file for complete search history.

(56) References Cited

U.S. PATENT DOCUMENTS

| | | | |
|---|---|---|---|
| 9,398,887 B2 | 7/2016 | Miyazawa | ............. A61B 6/463 |
| 2002/0099853 A1* | 7/2002 | Tsujii | ....................... H04L 29/06 |
| | | | 709/247 |

(Continued)

FOREIGN PATENT DOCUMENTS

JP 2002-209890 7/2002

*Primary Examiner* — Jon Chang
(74) *Attorney, Agent, or Firm* — Venable LLP

(57) ABSTRACT

An image generating apparatus comprises an information acquiring unit that acquires request information including information representing a viewing time and information representing image qualities; a control unit that sets the image qualities to the image qualities specified by the request information when the plurality of images can be generated with the image qualities specified by the request information before the viewing time passes, and sets the image qualities by changing the image qualities from the image qualities specified by the request information, otherwise; and a generating unit that generates the plurality of images with the image qualities set by the control unit.

10 Claims, 12 Drawing Sheets

(51) Int. Cl.
*G16H 40/63* (2018.01)
*A61B 5/145* (2006.01)

(56) References Cited

U.S. PATENT DOCUMENTS

2014/0107462 A1* 4/2014 Wanda ............... A61B 8/54
                                                     600/407
2016/0296120 A1* 10/2016 Miyasa ............ A61B 5/0095
2018/0168554 A1* 6/2018 Song ................. A61B 8/00

* cited by examiner

| PROTOCOL | PORTION | BREASTS (LEFT AND RIGHT) | | { 402 |
|---|---|---|---|---|
| | TO-BE-GENERATED IMAGES | TYPE OF IMAGE | IMAGE GENERATION PARAMETER | { 403 } 401 |
| | | TOTAL AMOUNT OF HEMOGLOBIN | ACCURACY LEVEL 4 | |
| | | OXYGEN SATURATION | ACCURACY LEVEL 4 | |
| PATIENT INFORMATION | MEDICAL CHECKUP/OUTPATIENT | | | { 404 |

FIG.4

| | | |
|---|---|---|
| REQUESTED VIEWING TIME | 11:00 NEXT MORNING | ⎫ 501 |
| OMISSION METHOD AT FIRST STAGE | GENERATE ALL IMAGES WITH UNIFORMLY REDUCED ACCURACIES | ⎫ 502 |
| EXECUTION OF SECOND STAGE | YES | ⎫ 503 |
| TO-BE-GENERATED IMAGES | TYPE OF IMAGE / IMAGE GENERATION PARAMETER (504a) / PRIORITY (504b) | ⎫ 504 |

| TYPE OF IMAGE | IMAGE GENERATION PARAMETER | PRIORITY |
|---|---|---|
| TOTAL AMOUNT OF HEMOGLOBIN | ACCURACY LEVEL 4 | HIGH |
| OXYGEN SATURATION | ACCURACY LEVEL 4 | LOW |

FIG.5

| PATIENT INFORMATION | REQUESTED VIEWING TIME |
|---|---|
| MEDICAL CHECKUP | NEXT MORNING |
| INPATIENT | AFTER 2 HOURS |
| OUTPATIENT | AFTER 20 MINUTES |

FIG.6A

| PATIENT INFORMATION | EXECUTION OF SECOND STAGE |
|---|---|
| SECONDARY TEST AFTER MEDICAL CHECKUP | YES |
| OTHERS | NO |

FIG.6B

| PATIENT INFORMATION | OMISSION METHOD AT FIRST STAGE |
|---|---|
| MEDICAL CHECKUP | WITH UNIFORMLY REDUCED ACCURACIES |
| INPATIENT | FOR ONLY IMAGE WITH HIGH PRIORITY |
| OUTPATIENT | WITH WEIGHTED ACCURACY |

FIG.6C

| PATIENT INFORMATION | PORTION | TYPE OF IMAGE | IMAGE GENERATION PARAMETER | PRIORITY |
|---|---|---|---|---|
| MEDICAL CHECKUP | BREAST | TOTAL AMOUNT OF HEMOGLOBIN | ACCURACY LEVEL 4 | 3 |
| | | OXYGEN SATURATION | ACCURACY LEVEL 4 | 1 |
| OUTPATIENT | BREAST | TOTAL AMOUNT OF HEMOGLOBIN | ACCURACY LEVEL 4 | 2 |
| | | OXYGEN SATURATION | ACCURACY LEVEL 4 | 2 |

FIG.6D

| TYPE OF IMAGE | IMAGE GENERATION PARAMETER |
|---|---|
| TOTAL AMOUNT OF HEMOGLOBIN | ACCURACY LEVEL 4 |

FIG.8A

| TYPE OF IMAGE | IMAGE GENERATION PARAMETER |
|---|---|
| TOTAL AMOUNT OF HEMOGLOBIN | ACCURACY LEVEL 2 |
| OXYGEN SATURATION | ACCURACY LEVEL 2 |

FIG.8B

| TYPE OF IMAGE | IMAGE GENERATION PARAMETER |
|---|---|
| TOTAL AMOUNT OF HEMOGLOBIN | ACCURACY LEVEL 3 |
| OXYGEN SATURATION | ACCURACY LEVEL 1 |

FIG.8C

| PATIENT INFORMATION | REQUESTED VIEWING TIME |
|---|---|
| EMERGENCY | AFTER 5 MINUTES |
| NON-EMERGENCY | AFTER 2 HOURS |

FIG.11

IMAGE GENERATING APPARATUS AND CONTROL METHOD THEREFOR

BACKGROUND OF THE INVENTION

Field of the Invention

The present invention relates to an image generating apparatus and a control method therefor.

Description of the Related Art

Mainly in the medical field, active research has been conducted on a photoacoustic apparatus which obtains information related to an object on the basis of acoustic waves (photoacoustic waves) generated by irradiating the object with light. By repeatedly irradiating the object with light at varied positions and reconstructing acquired photoacoustic signals, three-dimensional information of the object can be obtained. In addition, it has become prevalent to use the three-dimensional information acquired on the basis of the photoacoustic waves for diagnosis.

There is a trade-off relationship between the time spent to generate an acoustic wave image and the image quality. In other words, as more time is spent to generate the acoustic wave image, the image quality can be increased. The same applies also to the reconstruction of the acoustic wave image from photoacoustic signals in a photoacoustic imaging apparatus. In particular, the reconstruction of three-dimensional information involves a large amount of data and, depending on the content of processing, time as long as several to several tens of hours is needed. Accordingly, to make use of an acoustic wave image reconstructed from the three-dimensional information for diagnosis, it is desired to eliminate the trade-off.

For example, in the invention described in Japanese Patent Application Publication No. 2002-209890, in an ultrasound imaging apparatus, the density of the sampled points to be measured or the density of image data used when image reconstruction is performed is varied to change the resolution of a three-dimensional image. This allows the time required to display the image to be adjusted.

SUMMARY OF THE INVENTION

However, in the invention described above, the time spent to generate an acoustic wave image and the image quality may not necessarily be appropriate. For example, when a high-quality acoustic wave image is required after the generation of a low-quality acoustic wave image, an acoustic wave image has to be generated again.

When a high-quality acoustic wave image is generated, a long time is needed to generate the acoustic wave image. Consequently, the acquisition of a test result may be delayed longer than necessary. This may result in an inefficient diagnostic work flow depending on the settings of the time spent to generate an acoustic wave image and the image quality.

The present invention has been achieved in view of the foregoing problem. An object of the present invention is to provide an efficient work flow by generating an image having an appropriate image quality in accordance with a test situation.

The present invention in its one aspect provides an image generating apparatus generating a plurality of images by using a reception signal of an acoustic wave propagated from an object, the image generating apparatus comprising an information acquiring unit configured to acquire request information including information representing a viewing time requesting view of the plurality of images and information representing image qualities requested of the plurality of images; a control unit configured to set the image qualities of the plurality of images to the image qualities specified by the request information when the plurality of images can be generated with the image qualities specified by the request information before the viewing time passes, and set the image qualities of the plurality of images by changing the image qualities of the plurality of images from the image qualities specified by the request information when the plurality of images cannot be generated with the image qualities specified by the request information before the viewing time passes; and a generating unit configured to generate the plurality of images with the image qualities of the plurality of images set by the control unit.

The present invention in its another aspect provides an image generating apparatus generating a plurality of images by using a reception signal of an acoustic wave propagated from an object, the image generating apparatus comprising an information acquiring unit configured to acquire request information including information representing a viewing time requesting view of the plurality of images and information representing image qualities requested of the plurality of images; a control unit configured to set the image qualities of the plurality of images to the image qualities specified by the request information when the plurality of images can be generated with the image qualities specified by the request information before the viewing time passes, request a user to input information representing the image qualities of the plurality of images when the plurality of images cannot be generated with the image qualities specified by the request information before the viewing time passes, and set the image qualities of the plurality of images input by the user; and a generating unit configured to generate the plurality of images with the image qualities of the plurality of images set by the control unit.

The present invention in its another aspect provides a control method for an image generating apparatus generating a plurality of images by using a reception signal of an acoustic wave propagated from an object, the control method comprising acquiring request information including information representing a viewing time requesting view of the plurality of images and information representing image qualities requested of the plurality of images; setting the image qualities of the plurality of images to the image qualities specified by the request information when the plurality of images can be generated with the image qualities specified by the request information before the viewing time passes, setting the image qualities of the plurality of images by changing the image qualities of the plurality of images from the image qualities specified by the request information when the plurality of images cannot be generated with the image qualities specified by the request information before the viewing time passes; and generating the plurality of images with the set image qualities of the plurality of images.

The present invention in its another aspect provides a control method for an image generating apparatus generating a plurality of images by using a reception signal of an acoustic wave propagated from an object, the control method comprising acquiring request information including information representing a viewing time requesting view of the plurality of images and information representing image qualities requested of the plurality of images; setting the image qualities of the plurality of images to the image qualities specified by the request information when the plurality of images can be generated with the image qualities specified by the request information before the viewing time passes, requesting a user to input information representing the image qualities of the plurality of images when the plurality of images cannot be generated with the image qualities specified by the request information before the viewing time passes; setting the image qualities of the plurality of images input by the user; and generating the plurality of images with the set image qualities of the plurality of images.

According to the present invention, by generating an image having an appropriate image quality in accordance with a test situation, an efficient work flow can be provided.

Further features of the present invention will become apparent from the following description of exemplary embodiments with reference to the attached drawings.

BRIEF DESCRIPTION OF THE DRAWINGS

FIG. 4 is a view showing an example of information included in an order;

FIG. 5 is a view showing the items included in image viewing request information in the form of a table;

FIGS. 6A to 6D are views showing examples of rules for generating the image viewing request information;

FIGS. 8A to 8C are views each showing an example of an image generation method at a first stage;

FIG. 11 is a view showing an example of a rule for generating image viewing request information.

DESCRIPTION OF THE EMBODIMENTS

Figure 1:
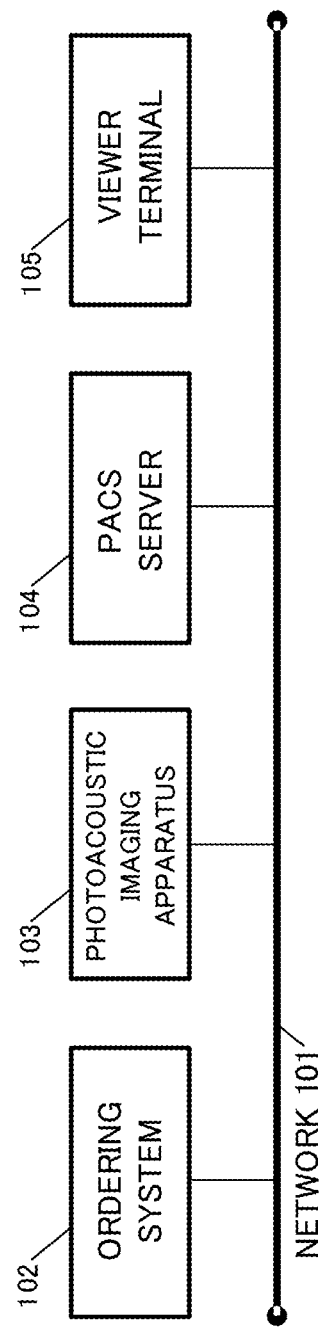
FIG. 1 is a view showing a network configuration of a whole system.

Referring to the drawings, the following will describe preferred embodiments of the present invention. However, the dimensions, materials, and shapes of components described below, relative positioning thereof, and the like are to be appropriately changed in accordance with a configuration of an apparatus to which the invention is applied and various conditions and are not intended to limit the scope of the invention to the following description.

The present invention relates to a technique which detects acoustic waves propagated from an object to generate and acquire the characteristic information of the inner portions of the object. Accordingly, the present invention is considered to be an acoustic wave image generating apparatus or a control method therefor, or a signal processing method. The present invention is also considered to be a program for causing an information processing device including hardware resources such as a CPU and a memory to implement each of the foregoing methods, or a non-transitory storage medium which can be read by a computer storing the program.

The acoustic wave image generating apparatus of the present invention includes an apparatus using a photoacoustic effect which irradiates an object with light (an electromagnetic wave) to receive acoustic waves generated in the object and acquire the characteristic information of the object as image data. In this case, the characteristic information is information on characteristic values corresponding to a plurality of respective positions in the object which are generated using reception signals obtained by receiving photoacoustic waves.

The characteristic information (photoacoustic characteristic information) derived from electric signals (photoacoustic signals) acquired by photoacoustic measurement is a value reflecting the absorptance of light energy. The characteristic information includes, e.g., the source of an acoustic wave generated by irradiation with light and an initial sound pressure in the object or a light energy absorption density and an absorption coefficient which are derived from the initial sound pressure and the concentration of a substance forming a tissue. By obtaining an oxygenated hemoglobin concentration and a deoxygenated hemoglobin concentration as the substance concentration, an oxygen saturation distribution can be calculated. As the substance concentration, a glucose concentration, a collagen concentration, a melanin concentration, a volume fraction of fat or water, or the like can also be obtained.

The acoustic wave image generating apparatus of the present invention also includes an apparatus using an ultrasonographic technique which transmits an ultrasound wave to an object to receive a reflection wave (echo wave) resulting from the reflection of the ultrasound wave from the inner portion of the object and acquire object information as image data. Characteristic information (ultrasound characteristic information) derived from an electric signal (ultrasound echo signal) acquired by an ultrasonographic apparatus reflects the acoustic impedance difference between the tissues of the inner portion of the object.

On the basis of characteristic information from each position in the object, a two-dimensional or three-dimensional characteristic information distribution can be obtained. Distribution data can be generated as image data. The characteristic information may also be obtained not as numerical value data, but as distribution information of each position in the object. Specific examples of the distribution information include an initial sound pressure distribution, an energy absorption density distribution, an absorption coefficient distribution, and an oxygen saturation distribution. Besides, an acoustic impedance distribution, distribution information representing a blood flow, or the like can also be generated. Since information based on an acoustic wave is thus visualized, the present invention can also be considered to be an acoustic wave imaging apparatus, a control method therefor, or a program.

The acoustic wave mentioned in the present invention is typically an ultrasound wave and includes an elastic wave referred to as a sound wave or an acoustic wave. An electric signal into which an acoustic wave is converted by a probe or the like is referred to also as an acoustic signal. However, the ultrasound wave or acoustic wave recited in the present specification is not intended to limit the wavelength of such an elastic wave. The acoustic wave generated by a photoacoustic effect is referred to as a photoacoustic wave or an optical ultrasound wave. An electric signal derived from a photoacoustic wave is referred to also as a photoacoustic signal. An electric signal derived from an echo wave resulting from the reflection of a transmission ultrasound wave by the object is referred to also as an ultrasound echo signal.

In each of the cases where the apparatus of the present invention receives a photoacoustic wave, where the apparatus of the present invention receives an ultrasound echo, and where the apparatus of the present invention receives both of a photoacoustic wave and an ultrasound echo, the apparatus invariably generates an image on the basis of the acoustic wave received thereby. Accordingly, the apparatus of the present invention can also be referred to as an acoustic wave image generating apparatus. The present invention can also be considered to be a control method for such an acoustic wave image generating apparatus.

[Embodiment 1]

(System Configuration)

FIG. 1 is a view showing a network configuration of a whole system. The following is a description of each of the components in FIG. 1. A network 101 is a computer network connecting individual nodes 102 to 105 to each other. The network 101 shown in FIG. 1 is a bus-type network, but is not limited thereto. The network 101 may also be a network of another type.

Each of the nodes 102 to 105 transmits/receives an order and an image to/from another node through the network 101.

The ordering system 102 has the function of issuing an order to a photoacoustic imaging apparatus 103. The order is information for requesting a test of the photoacoustic imaging apparatus 103. The ordering system 102 includes a computer terminal. A medical doctor inputs information related to a test for a patient from the computer terminal. The computer terminal receives the input of the information related to the order from the medical doctor who requests the test and issues the order.

In Embodiment 1, a description will be given of an example in the case where it is possible to routinely specify test items on the basis of patient information, such as in the case of medical checkup or normal outpatient. In such a case, the ordering system 102 can issue an order on the basis of the patient information.

By contrast, in Embodiment 2 described later, a description will be given of an example in the case where it is impossible to specify test items on the basis of patient information, such as in the case of emergency outpatient. In such a case, the ordering system 102 cannot issue an order on the basis of the patient information. Accordingly, the ordering system 102 requests the medical doctor to input an order.

However, ordering is not limited to the cases in Examples 1 and 2. The ordering system 102 may also request the medical doctor to input an order for a predetermined item.

The photoacoustic imaging apparatus 103 has the function of generating images on the basis of acoustic waves propagated from an object. An imaging technologist operates the photoacoustic imaging apparatus 103 so as to perform an intended test on the patient. The photoacoustic imaging apparatus 103 is operated by the imaging technologist to image an object 210 as the target portion of the patient. The photoacoustic imaging apparatus 103 transmits an images obtained by the imaging to a PACS server 104.

The picture archiving and communication system (PACS) server 104 stores the images received from the photoacoustic imaging apparatus 103 in a storage region. The PACS mentioned herein refers to a medial image management system for storing, viewing, and managing medical image data such as CT, CR, and MRI image data. Medical images can be viewed from the terminal connected to the PACS.

A viewer terminal 105 displays the images acquired from the PACS server 104 on a screen. A radiogram interpreting doctor diagnoses the target portion of the patient on the basis of the images displayed by the viewer terminal 105. The radiogram interpreting doctor views the screen displayed on the viewer terminal 105 to diagnose the patient. Note that the radiogram interpreting doctor may also be the same person as the medical doctor who operates the ordering system 102.

Each of the ordering system 102, the PACS server 104, and the viewer terminal 105 is implemented by a typical computer system. That is, each of the components thereof may include a central processing unit (CPU), a GPU, a random access memory (RAM), a hard disc drive and a network interface. Each of the components thereof may also include a keyboard, a mouse, and a liquid crystal display. The CPU (GPU) reads out the program recorded in the hard disc drive, develops the program in the RAM, and executes the program to execute processing.

Figure 2:
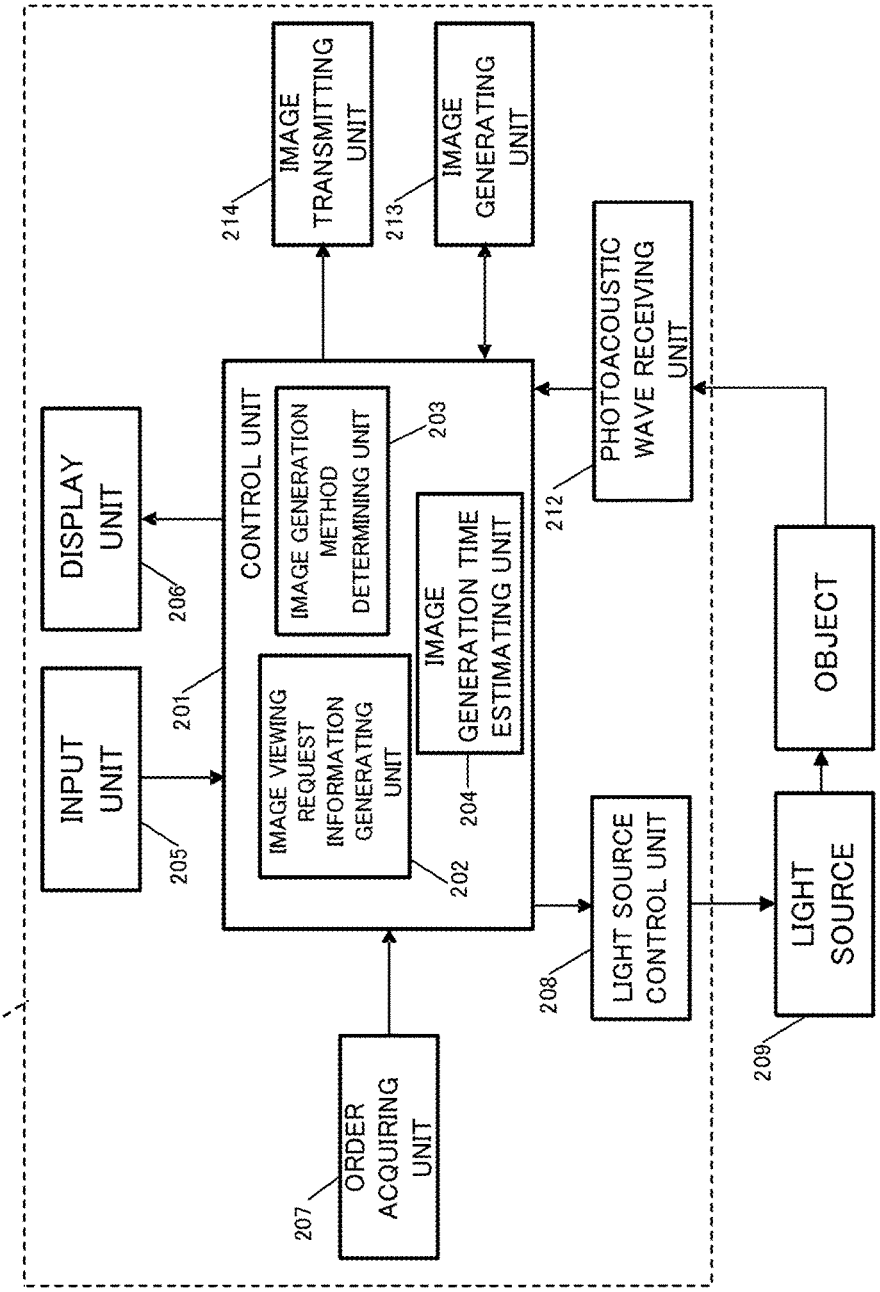
FIG. 2 is a view showing the components of a photoacoustic imaging apparatus.

FIG. 2 is a view showing the components of the photoacoustic imaging apparatus 103. The photoacoustic imaging apparatus 103 has a control unit 201, an input unit 205, a display unit 206, an order acquiring unit 207, a light source control unit 208, a photoacoustic wave receiving unit 212, an image generating unit 213, and an image transmitting unit 214. The following is a description of each of the processing units.

The control unit 201 has the function of controlling each of the processing units. The control unit 201 has an image viewing request information generating unit 202, an image generation method determining unit 203, and an image generation time estimating unit 204.

The image viewing request information generating unit 202 has the function of generating image viewing request information on the basis of the order acquired by the order acquiring unit 207. The image viewing request information is the information required for images to be generated. For example, the image viewing request information includes items such as a requested viewing time, the qualities of images to be generated, and the priorities of the images to be generated. Note that the image viewing request information generating unit 202 is an example of an information acquiring unit.

The image generation method determining unit 203 has the function of determining an image generation method on the basis of the image viewing request information generated by the image viewing request information generating unit 202.

The image generation method determining unit 203 inquires at the image generation time estimating unit 204 to acquire the time required for image generation. The image generation method determining unit 203 determines the image generation method on the basis of the image viewing request information and the time required for image generation. Note that the details of the determination of the image generation method will be described later.

The image generation time estimating unit 204 has the function of estimating the time required for image generation from the image viewing request information generated by the image viewing request information generating unit 202.

The input unit 205 receives the settings and request made to the photoacoustic imaging apparatus 103 which are input by the radiogram interpreting doctor, the imaging technologist, or the like. For example, the input unit 205 receives an instruction to the photoacoustic imaging apparatus 103 which is input by the imaging technologist.

The display unit 206 displays the state of the photoacoustic imaging apparatus 103 or the generated image. In the following, the input unit 205 and the display unit 206 may be referred to as a user interface. The display unit 206 displays the generated image data. As the display unit 206, any display device such as a liquid crystal display or an organic EL display can be used. The display unit 206 may be provided integrally with or separately from the photoacoustic imaging apparatus 103.

The order acquiring unit 207 has the function of acquiring an order from the ordering system 102.

The light source control unit 208 controls the direction of measurement light emitted for irradiation from a light source 209 or the like. As the light source, a laser capable of producing a high output is preferred. However, a flash lamp, a light emitting diode, or the like can also be used. The light source 209 applies predetermined pulsed light to an object. The light source 209 supplies light energy to the object to cause the object to generate photoacoustic waves. When the object is a living body, the light source 209 emits irradiating light at a specified wavelength which is absorbed by a specified one of the components forming a breast. The light source 209 may be provided integrally with the photoacoustic imaging apparatus 103 in the present embodiment or may also be provided alone as a separate body. As the light source 209, a pulsed light source capable of generating pulsed light on the order of several to several hundreds of nanoseconds as irradiating light is preferred. Specifically, to efficiently generate photoacoustic waves, a pulse width of about 10 to 100 nanoseconds is used.

The photoacoustic wave receiving unit 212 has the function of receiving the photoacoustic waves generated from the object and converting the photoacoustic waves into photoacoustic signals. For example, the photoacoustic wave receiving unit 212 has a probe including a piezoelectric element. In the photoacoustic wave receiving unit 212, a plurality of receiving elements (not shown) which receive photoacoustic waves are disposed. At this time, when at least some of the receiving elements are disposed such that the receiving surfaces (directivity axes) thereof are at different angles, a portion under test can be measured from different directions, which results in an improved image quality. In a more preferable form, the plurality of receiving elements may be disposed appropriately such that the receiving surfaces thereof face the center of a hemisphere.

The image generating unit 213 has the function of generating images from the photoacoustic signals acquired by the photoacoustic wave receiving unit 212. The image generating unit 213 may also perform a three-dimensional image reconstruction process. The image reconstruction process may also be a process based on, e.g., a phase shaping addition, a Fourier transformation method, a filtered back projection (FBP), or the like. The amount of data and the amount of calculation in the image generation process performed in the image generating unit 213 are large. Accordingly, the image generation process performed in the image generating unit 213 may also be implemented by parallel computation hardware such as a graphics processing unit (GPU).

The image transmitting unit 214 has the function of transmitting the images generated by the image generating unit 213 to the PACS server 104.

Of the components of the photoacoustic imaging apparatus 103, the control unit 201, the input unit 205, the display unit 206, the order acquiring unit 207, the image generating unit 213, and the image transmitting unit 214 are each implemented using a typical computer system. That is, the process in each of the processing units is performed by a central processing unit (CPU), a GPU, a random access memory (RAM), a hard disc drive, and a network interface. The photoacoustic imaging apparatus 103 has a bus connecting the individual components to each other.

The CPU (GPU) reads out the program recorded in the hard disc drive, develops the program in the RAM, and executes the program to thus execute the process in each of the foregoing processing units.

(Process Flow)

Figure 3:
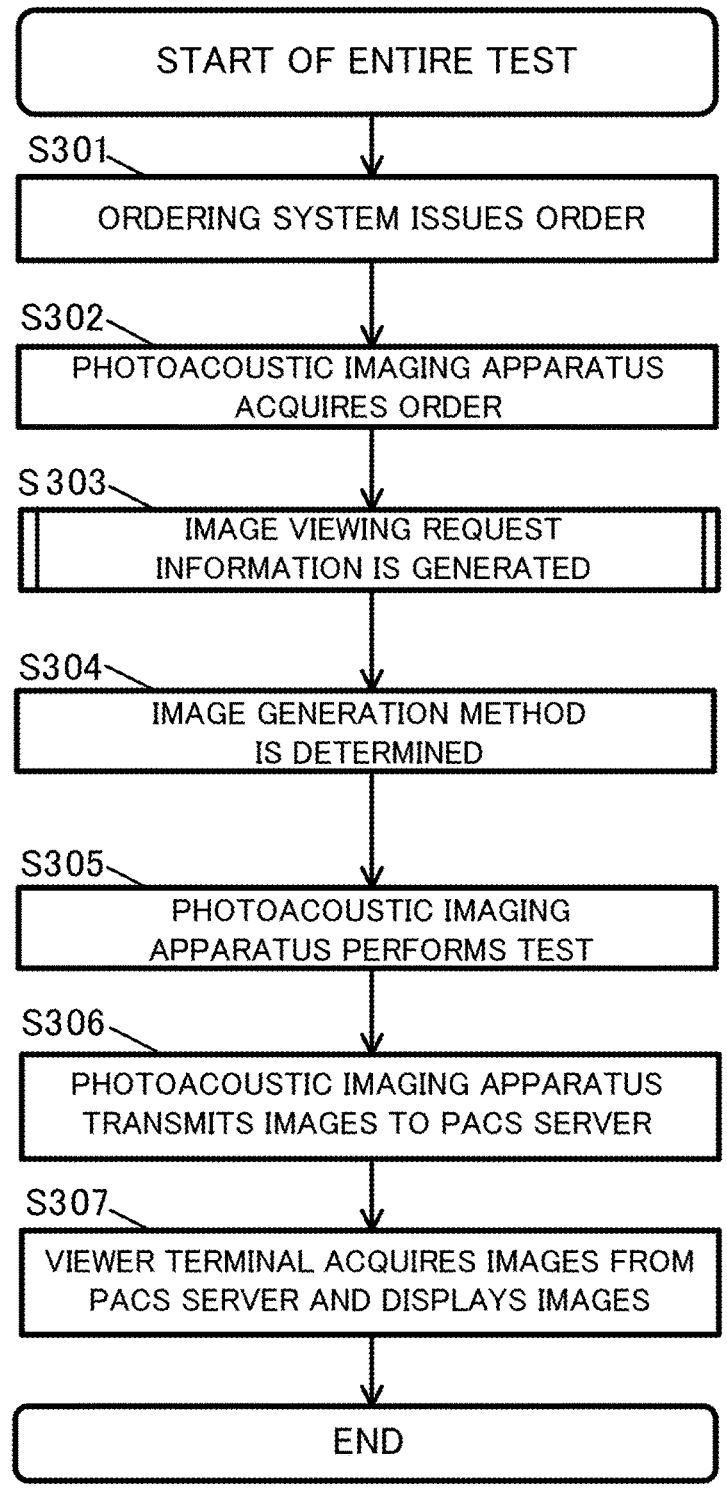
FIG. 3 is a view showing the overall flow of a test in Embodiment 1.

FIG. 3 is a view showing the overall flow of the test in Embodiment 1. The flow in FIG. 3 will be sequentially described. In S301, the ordering system 102 issues an order. Specifically, the ordering system 102 receives patient information such as general medical practice, medical checkup, or outpatient and information related to a test for a portion to be diagnosed or the like, which is input by the medical doctor or the like. The ordering system 102 generates the order on the basis of the received information.

In S302, the order acquiring unit 207 of the photoacoustic imaging apparatus 103 acquires the order issued from the ordering system 102.

FIG. 4 is a view showing an example of the information included in the order. As shown in FIG. 4, the order includes a protocol 401 and patient information 404. The protocol 401 is a combination of a portion 402 and to-be-generated images 403. The portion 402 shows a specification of the portion of a patient which is to be tested. For example, in the example in FIG. 4, breasts (left and right) are specified as the portion 402.

The to-be-generated mages 403 is a specification of the images to be generated in the test.

For example, in the example in FIG. 4, respective images of a total amount of hemoglobin and oxygen saturation are specified as the to-be-generated mages 403. To each of the to-be-generated images, an image generation parameter is set. For example, the image generation parameter is set on a 5-point scale of ACCURACY LEVELS 1 to 5 in increasing order of accuracy (image quality). In the example in FIG. 4, to the to-be-generated image of the total amount of hemoglobin, ACCURACY LEVEL 4 is set and, to the to-be-generated image of oxygen saturation, ACCURACY LEVEL 4 is set.

The patient information 404 is information about the patient to be tested. In the example in FIG. 4, the patient information 404 shows that the patient involved in this order gets a medical checkup and is an outpatient. The patient information 404 may also include an item such as first visit, medical checkup, secondary test after medical checkup, follow-up observation, outpatient, or inpatient. Note that the order shown in FIG. 4 is exemplary and may also include other elements. The patient information 404 is an example of a patient category.

Referring back to FIG. 3, the image viewing request information generating unit 202 generates the image viewing request information from the order in S303. The following will describe an example of the image viewing request information.

FIG. 5 is a view showing the items included in the image viewing request information in the form of a table. The image viewing request information has a first parameter 501 (REQUESTED VIEWING TIME), a second parameter 502 (OMISSION METHOD AT FIRST STAGE), a third parameter 503 (EXECUTION OF SECOND STAGE), and a fourth parameter 504 (TO-BE-GENERATED IMAGE). A description will be given of each of the items in FIG. 5.

The first parameter 501 (REQUESTED VIEWING TIME) represents the user-requested time (date and time) when a user can view the images on the viewer terminal 105. Note that the requested viewing time shown in the drawing is an example of a viewing time.

The second parameter 502 (OMISSION METHOD AT FIRST STAGE) represents a method for omitting the to-be-generated images at a first stage when it is expected that the requested viewing time will be missed if the images are generated exactly in accordance with the fourth parameter.

The second parameter 502 may also be set by the medical doctor or imaging technologist when it is expected that the requested viewing time will be missed. Alternatively, as will be described later, the second parameter 502 may also be set from the order on the basis of predetermined rules.

In the following description, "PARTIAL OMISSION OF IMAGE GENERATION" may be set to the second parameter 502.

The third parameter 503 (EXECUTION OF SECOND STAGE) represents whether or not a second-stage test is to be performed after the first stage of image generation is executed. The second-stage test is performed as a retest when, e.g., it is determined in a first-stage test that the possibility of finding an abnormality in the patient is high.

The fourth parameter 504 (TO-BE-GENERATED IMAGES) is related to the images intended to be generated. This item represents a request, not an instruction to generate the images exactly as it says. When it is expected that the requested viewing time will be missed if the images are generated exactly in accordance with the fourth parameter 504, "PARTIAL OMISSION OF IMAGE GENERATION" is performed in accordance with the second parameter 502.

An image generation parameter 504a is an image generation parameter for each of the images which is included in the fourth parameter. The image generation parameter 504a is set on a 5-point scale of ACCURACY LEVELS 1 to 5 in increasing order of accuracy (image quality). Note that the image generation parameter 504a corresponds to the image generation parameter in the order in FIG. 4.

A priority 504b represents the priority of each of the images. The priority 504b is used when the partial omission of image generation is performed. As will be described later, the priority 504b may also be set from the order on the basis of a predetermined rule.

The partial omission of image generation, which is specified as the second parameter 502, will be described.

For example, the image generation method determining unit 203 selects one of the following three generation methods on the basis of the image viewing request information and the time required for image generation.

(1) Generate only the image with a high priority.

When this generation method is selected, the image generating unit 213 generates only the image with the high priority 504b, and does not generate the image with the low priority 504b.

(2) Generate all the images with uniformly reduced accuracies.

When this generation method is selected, the image generating unit 213 generates each of the images by uniformly reducing the accuracies of the image generation parameters 504a of all the to-be-generated images. The image generating unit 213 may also generate the images with accuracies as high as possible within the range in which the requested viewing time is not missed.

(3) Generate the images with accuracies weighted by the priorities of the images.

When this generation method is selected, the image generating unit 213 generates the images by reducing the degree to which the accuracy of the image generation parameter 504a is reduced for the to-be-generated image with the high priority 504b. The image generating unit 213 also generates the images by increasing the degree to which the accuracy of the image generation parameter 504a is reduced for the to-be-generated image with the low priority 504b.

By selecting one of the generation methods (1) to (3) as the second parameter 502, "PARTIAL OMISSION OF IMAGE GENERATION" is performed so that the images are generated before the requested viewing time.

The choices to be selected shown above are exemplary. These choices may also be used compositely or another choice to be selected not to miss the requested viewing time may also be provided.

The image viewing request information generating unit 202 generates the image viewing request information from the order on the basis of the predetermined rules recorded on a hard disc.

Examples of the rules for generating the image viewing request information will be shown below.

FIGS. 6A to 6D are views showing the examples of the rules for generating the image viewing request information in Embodiment 1.

FIG. 6A shows the example of the rule for setting the first parameter (REQUESTED VIEWING TIME) from the patient information 404. When the patient information 404 includes "MEDICAL CHECKUP", it is sufficient for the image viewing request information generating unit 202 to give a notice representing the result of the medical checkup at a later date. Accordingly, the requested viewing time is set to "11:00 NEXT MORNING". When the patient information 404 includes "INPATIENT", the image viewing request information generating unit 202 sets the requested viewing time to "AFTER 2 HOURS", since a retest is easy. When the patient information 404 includes "outpatient", the image viewing request information generating unit 202 sets the requested viewing time to "AFTER 20 MINUTES" to allow the images to be checked before the patient goes home.

For example, in the example in FIG. 4, the patient information 404 includes "MEDICAL CHECKUP" and "OUTPATIENT". In such a case, the image viewing request information generating unit 202 sets the requested viewing time (FIG. 5) to "11:00 NEXT MORNING" for "MEDICAL CHECKUP", which is later in time.

FIG. 6B shows the example of the rule related to the correspondence between the patient information 404 and the third parameter 503 (EXECUTION OF SECOND STAGE). When the patient information 404 includes "SECONDARY TEST AFTER MEDICAL CHECKUP", it is clear that suspicion of disease is high and the result of the test needs to be examined later. Accordingly, the image viewing request information generating unit 202 sets the third parameter to "YES". Otherwise, the image viewing request information generating unit 202 sets the third parameter to "NO".

For example, in the example in FIG. 4, the patient information 404 includes "MEDICAL CHECKUP". Accordingly, the image viewing request information generating unit 202 sets the third parameter ("EXECUTION OF SECOND STAGE" in FIG. 5) to "YES".

FIG. 6C shows the example of the rule related to the correspondence between the patient information 404 and the second parameter 502 (OMISSION METHOD AT FIRST STAGE).

For example, when the patient information 404 includes "MEDICAL CHECKUP", it is necessary to output all the images. Accordingly, the image viewing request information generating unit 202 sets the second parameter to "Generates all the images with uniformly reduced accuracies (WITH UNIFORMLY REDUCED ACCURACIES)".

When the patient information 404 includes "INPATIENT", the image viewing request information generating unit 202 sets the second parameter to "Generate only the image with a high priority (FOR ONLY IMAGE WITH HIGH PRIORITY)".

When the patient information 404 includes "OUTPATIENT", the image viewing request information generating unit 202 sets the second parameter to "Generate images with accuracies weighted by the priorities of the images (FOR ONLY IMAGE WITH HIGH PRIORITY)".

Note that, when the patient information 404 includes "MEDICAL CHECKUP" and "OUTPATIENT" as in the example in FIG. 4, it may also be possible to prioritize "MEDICAL CHECKUP" and appropriately use "Generate all the images with uniformly reduced accuracies (WITH UNIFORMLY REDUCED ACCURACIES)".

FIG. 6D shows the relationship between each of the patient information 404 and the portion 402, and the to-be-generated images 403. For example, when the patient information 404 is "MEDICAL CHECKUP" and the portion 402 is "BREAST", the image viewing request information generating unit 202 sets the types of the images to "TOTAL AMOUNT OF HEMOGLOBIN" and "OXYGEN SATURATION". The image viewing request information generating unit 202 also sets the respective image generation parameters 504a of the to-be-generated images to "ACCURACY LEVEL 4" and "ACCURACY LEVEL 4" and sets the respective priorities 504b of the to-be-generated images to "3" and "1". When the patient information 404 is "OUTPATIENT" and the portion 402 is "BREAST", the image viewing request information generating unit 202 sets the types of the images and the image generation parameter 504a in the same manner as when the patient information 404 is "MEDICAL CHECKUP". The image viewing request information generating unit 202 also sets the respective priorities 504b of the to-be-generated images to "2" and "2".

Note that FIGS. 6A to 6D are exemplary, and another rule may also be defined.

Referring back to FIG. 3, in Step S304, the image generation method determining unit 203 determines the image generation method on the basis of the image viewing request information. The flow of the process of determining the image generation method will be described later.

In Step S305, the image generating unit 213 generates images on the basis of the photoacoustic signals received from the photoacoustic wave receiving unit 212 in accordance with the determined image generation method. The image generation method includes determining, for each of the to-be-generated images, whether or not the image is to be generated and the image processing parameter (accuracy).

In S306, the image transmitting unit 214 transmits the images to the PACS server 104. The PACS server 104 stores the transmitted images.

In S307, the viewer terminal 105 acquires the images from the PACS server 104 and displays the images. The radiogram interpreting doctor can view the images displayed on the viewer terminal 105 and make a diagnosis.

Figure 7:
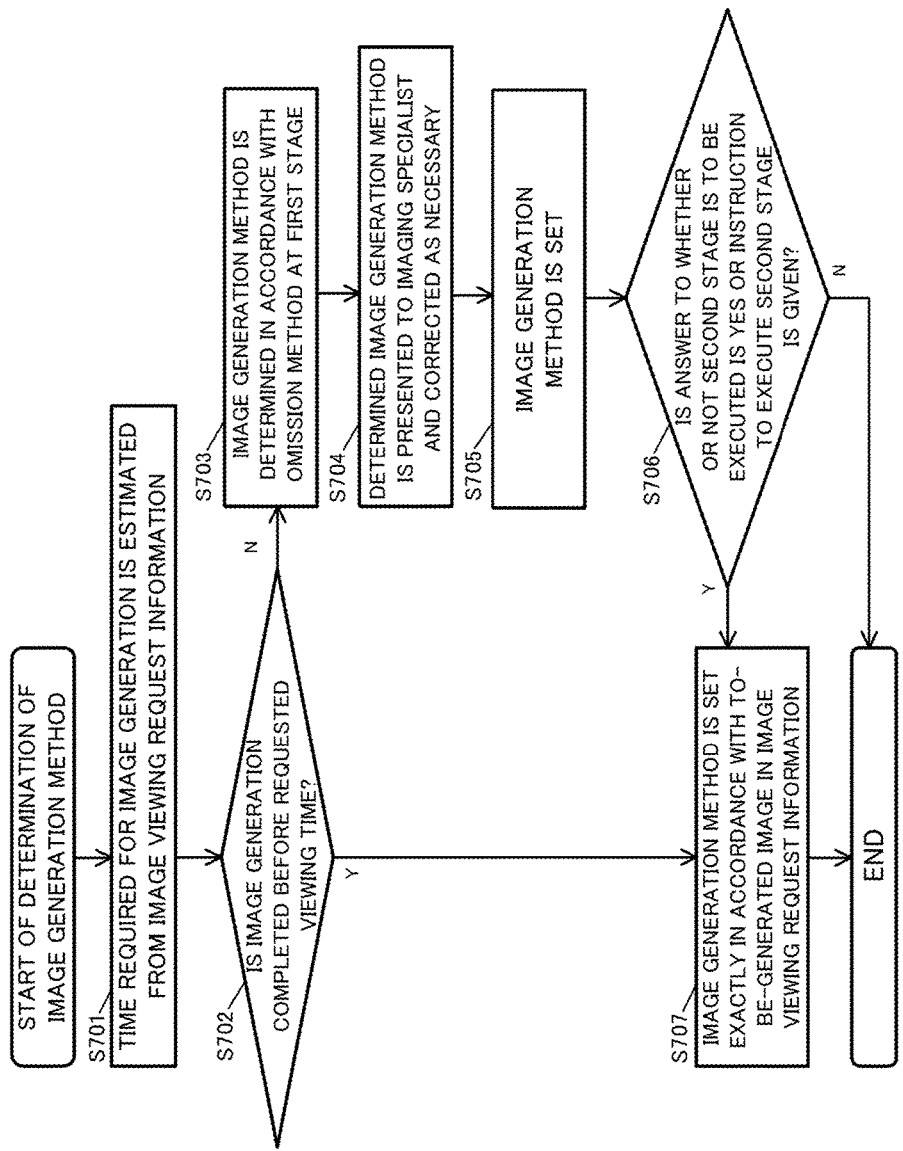
FIG. 7 is a view showing an example of the flow of the process of determining an image generation method.

FIG. 7 is a view showing an example of the flow of the process of determining the image generation method on the basis of the image viewing request information. FIG. 7 is a flow chart corresponding to the process in Step S304 in FIG. 3.

In S701, the image generation time estimating unit 204 estimates the time required for image generation from the image viewing request information generated by the image viewing request information generating unit 202. Specifically, the image generation time estimating unit 204 calculates the time required for image generation on the basis of the accuracy of each of the images represented by the image generation parameter 504a in the image viewing request information.

In S702, the image generation method determining unit 203 determines whether or not image generation is completed before the requested viewing time. Specifically, the image generation method determining unit 203 adds up the time required for image generation estimated by the image generation time estimating unit 204 and the current time to calculate an estimated image generation completion time. Subsequently, the image generation method determining unit 203 compares the estimated image generation completion time to the requested viewing time to determine whether or not image generation is completed before the requested viewing time.

When determination has been made that image generation is completed before the requested image viewing time (YES in Step S702), the image generation method determining unit 203 moves to the process in Step S707. On the other hand, when determination has been made that image generation is not completed before the requested image viewing time (NO in Step S702), the image generation method determining unit 203 moves to the process in Step S703.

In Step S703, the image generation method determining unit 203 determines the image generation method at the first stage when "PARTIAL OMISSION OF IMAGE GENERATION" is performed in accordance with the second parameter.

A description will be given of the case where, e.g., the second parameter is one of "(1) Generate only the image with a high priority, (2) Generate all the images with uniformly reduced accuracies, and (3) Generate the images with accuracies weighted by the priorities of the images".

FIGS. 8A, 8B, and 8C are views each showing an example of the image generation method at the first stage. FIG. 8A shows the image generation method when the second parameter is "(1) Generate only the image with a high priority". The image generation method determining unit 203 determines that only the image of the total amount of hemoglobin with a high priority is to be generated at ACCURACY LEVEL 4.

FIG. 8B shows the image generation method when the second parameter is "(2) Generate all the images with uniformly reduced accuracies". The image generation method determining unit 203 determines that the accuracy of the image of the total amount of hemoglobin is to be reduced from ACCURACY LEVEL 4 to ACCURACY LEVEL 2, and the accuracy of the image of the oxygen saturation is to be reduced from ACCURACY LEVEL 4 to ACCURACY LEVEL 2.

FIG. 8C shows the image generation method when the second parameter is "(3) Generate the images with accuracies weighted by the priorities of the images". The image generation method determining unit 203 determines that the accuracy of the image of the total amount of hemoglobin with a high accuracy is to be reduced from ACCURACY LEVEL 4 to ACCURACY LEVEL 3, and the accuracy of the image of the oxygen saturation with a low priority is to be reduced from ACCURACY LEVEL 4 to ACCURACY LEVEL 1.

Referring back to FIG. 7, in S704, the display unit 206 presents the determined image generation method at the first stage to the imaging technologist.

Figure 9:
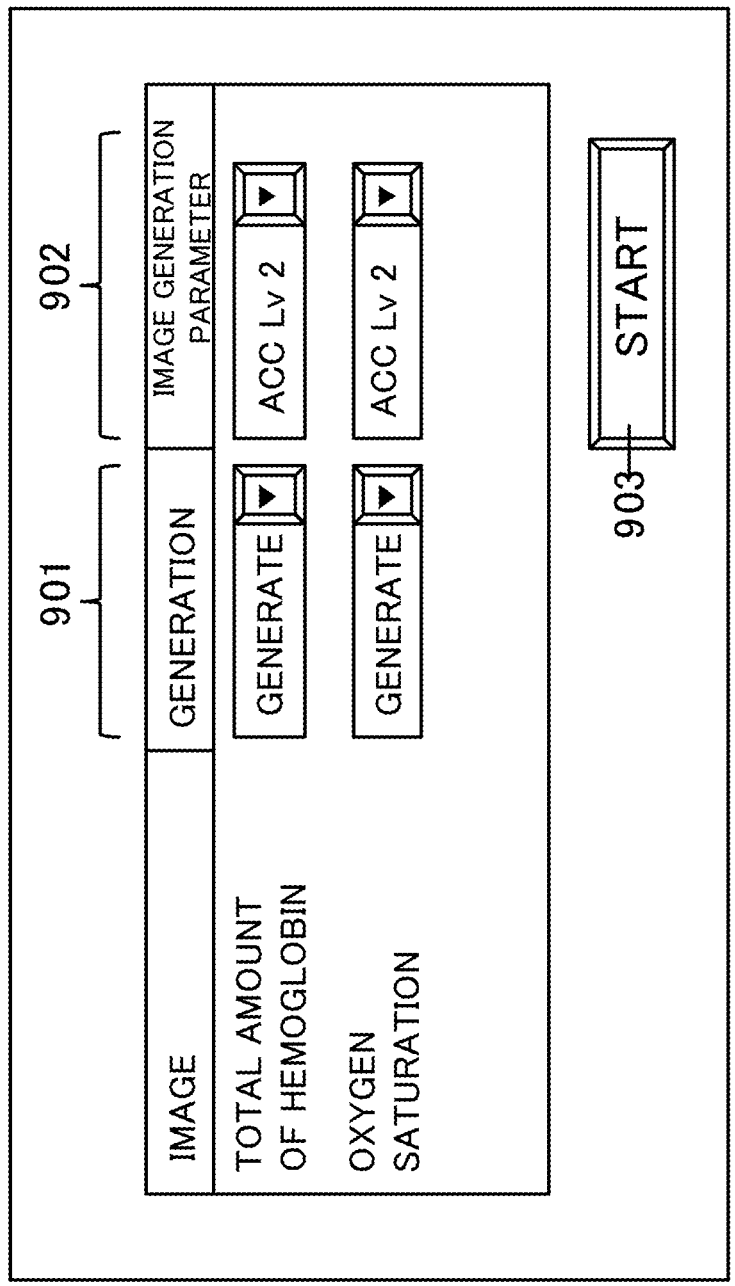
FIG. 9 is a view showing an example of the display of the image generation method at the first stage.

FIG. 9 is a view showing an example of the display of the image generation method at the first stage. FIG. 9 shows an example of the image formation method displayed on the display unit 206 when the second parameter is "(2) Generate all the images with uniformly reduced accuracies".

The display allows the imaging technologist to recognize whether or not "PARTIAL OMISSION OF IMAGE GEN- ERATION" is appropriately performed. When determination has been made that the image generation method at the first stage is not appropriate, the imaging technologist can correct the image generation method at the first stage using the input unit 205.

A description will be given of each of the portions of FIG. 9. An item 901 is an interface which displays whether or not each of the images is to be generated and receives a change. The item 901 is in the form of drop-down boxes. By developing each of the drop-down boxes, it is possible to select "GENERATE" or "DO NOT GENERATE".

An item 902 is an interface which displays the image generation parameter of each of the images and receives a change. The item 902 is in the form of drop-down boxes. By developing each of the drop-down boxes, it is possible to select among ACCURACY LEVELS (ACC Lv) 1 to 5.

When an image generation start button 903 is pressed down, the flow in FIG. 7 moves to S705.

Referring back to FIG. 7, in S705, the image generation method determining unit 203 sets the image generation method at the first stage of image generation. Subsequently, the image transmitting unit 214 transmits the content of the setting to the PACS server 104.

In S706, the image generation method determining unit 203 determines whether or not the current situation corresponds to either of the cases where the third parameter is "YES" and where an instruction to execute the second stage is given by the medical doctor. The instruction to execute the second stage may be acquired from the input unit 205 when, e.g., the medical doctor determines that the patient needs a retest.

When the current situation corresponds to either of the cases (YES in Step S706), the photoacoustic imaging apparatus 103 moves to the process in Step S707. On the other hand, when the current situation corresponds to neither of the cases, the photoacoustic imaging apparatus 103 ends the process of determining the image generation method.

In S707, the images are generated exactly in accordance with the fourth parameter set in the image viewing request information. Then, the images are transmitted to the PACS server 104. When the process moves from S704 to S705, image generation is at the second stage in S705. When the process moves from Step S706 to Step S707, the image generation method is overwritten.

Since there are various diagnoses, it takes a large amount of labor to set the generation method for each of the images in accordance with each of the diagnoses so as not to miss the requested viewing request. According to the present embodiment, by inputting minimum information, images with appropriate accuracies in accordance with situations can be generated.

In the description given in Embodiment 1, when the photoacoustic imaging apparatus 103 determines that image generation is not completed before the requested viewing time, the image quality is reset automatically, but the setting of the image quality is not limited thereto. For example, when determination has been made that image generation is not completed before the requested image viewing time, the photoacoustic imaging apparatus 103 may cause an input screen to be displayed and requests the user to input the accuracy of each of the images. Subsequently, the photoacoustic imaging apparatus 103 may also set the image quality on the basis of the information input by the user.

The photoacoustic imaging apparatus 103 may also determine a recommended value of the image quality (accuracy of the image) on the basis of the second parameter and display the recommended value on the input screen. This allows the medical doctor to know a standard image quality when setting the image quality, saves the trouble of recognizing the estimated image generation completion time, and contributes to an increase in the efficiency of the work flow.

[Embodiment 2]

In Embodiment 2, processing is performed on the basis of the order input by the user.

When test items cannot be specified on the basis of the patient information such as when, e.g., the patient is an emergency outpatient, the ordering system 102 cannot set the order on the basis of the patient information. As a result, the ordering system 102 requests the medical doctor to input the order. Note that the ordering system 102 may also set a part of the order even when the patient is an emergency outpatient.

The overall configuration of the system including the photoacoustic imaging apparatus and the content of the processing in Embodiment 2 are the same as in FIG. 1, except for the points shown below.

When the patient information 404 is "EMERGENCY", the ordering system 102 requests the imaging technologist to input the protocol 401. The order acquiring unit 207 receives the protocol 401 input via the input unit 205.

Note that, when an emergency patient is accepted, the patient information 404 is "EMERGENCY".

The image viewing request information generating unit 202 generates the image viewing request information from the protocol 401 input by the imaging technologist.

Figure 10:
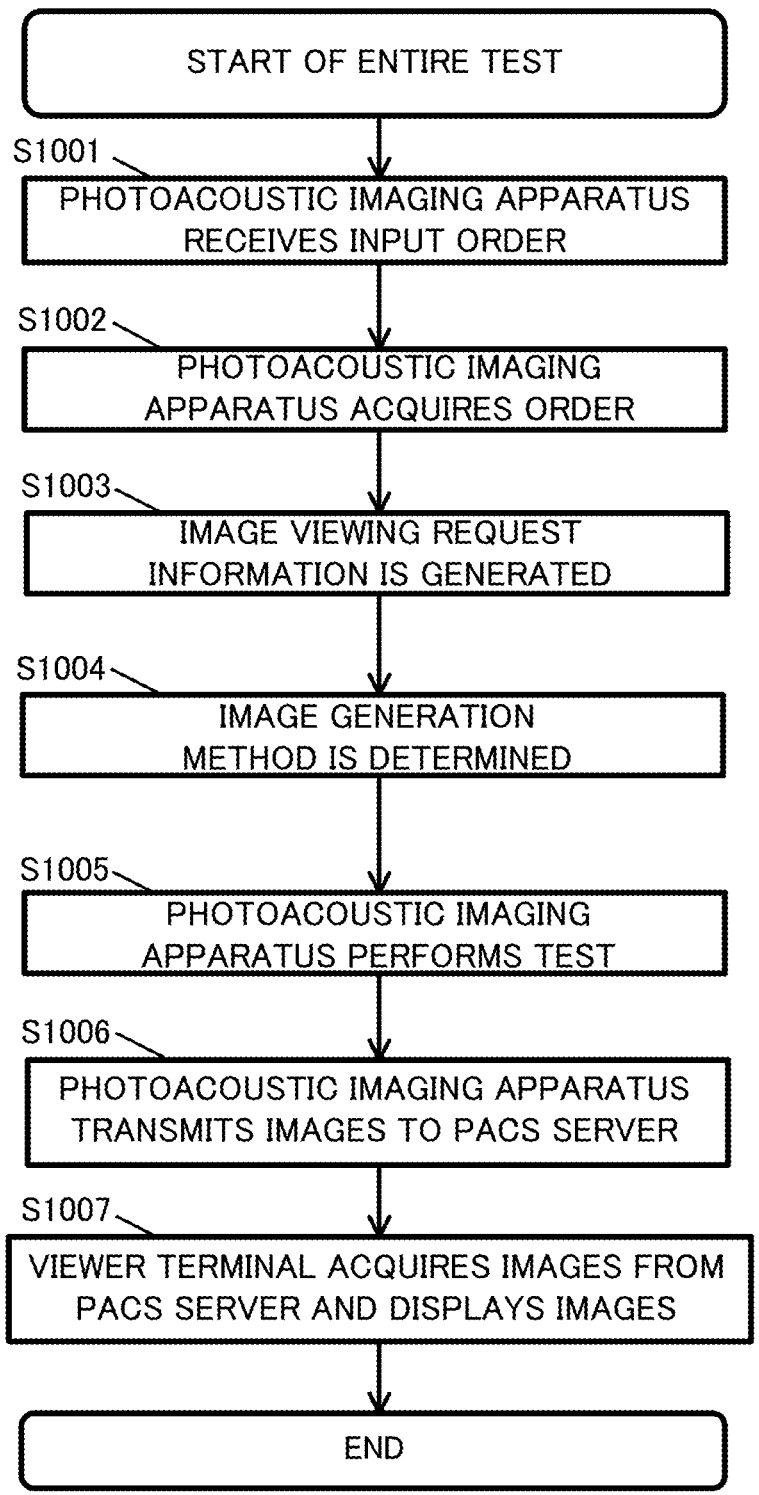
FIG. 10 is a view showing the overall flow of the test in Embodiment 2.

FIG. 10 is a view showing the overall flow of the test in Embodiment 2. In Step S1001, the photoacoustic imaging apparatus 103 receives the order input by the imaging technologist via the input unit 205. For example, when "EMERGENCY" is input as the patient information 404, the ordering system 102 displays a pop-up on the display unit 206 and requests the imaging technologist to input information such as the types of the images to be generated and the image generation parameters. Note that a user other than the imaging technologist may also input information.

In Step S1002, the photoacoustic imaging apparatus 103 acquires the order input by the imaging technologist.

In Step S1003, the image viewing request information generating unit 202 generates the image viewing request information generated from the order.

FIG. 11 is a view showing an example of a rule for generating the image viewing request information in Embodiment 2.

According to FIG. 11, when the patient information 404 is "EMERGENCY" representing that the patient is an emergency patient, the image viewing request information generating unit 202 sets the requested viewing time to "AFTER 5 MINUTES". In any other case, the image viewing request information generating unit 202 sets the requested viewing time to "AFTER 2 HOURS". Thus, when the patient is an emergency patient, early generation of the images is prioritized to the image quality.

In Step S1004, the image generation method determining unit 203 determines the image generation method on the basis of the image viewing request information.

In Step S1005, the image generating unit 213 generates the images on the basis of the photoacoustic signals received from the photoacoustic wave receiving unit 212 in accordance with the determined image generation method.

In Step S1006, the image transmitting unit 214 transmits the images to the PACS server 104. The PACS server 104 stores the transmitted images.

In Step S1007, the viewer terminal 105 acquires the images from the PACS server 104 and displays the images.

The radiogram interpreting doctor can view the images displayed on the viewer terminal 105 and make a diagnosis.

Thus, when the patient is an emergency patient, the emergency patient can flexibly be cared by allowing test items to be freely set by the medical doctor and generating the images so as not to miss the requested viewing time.

(Other Embodiments)

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-226067, filed on Nov. 21, 2016, which is hereby incorporated by reference herein in its entirety.

What is claimed is:

1. An image generating apparatus generating a plurality of images by using a reception signal of an acoustic wave propagated from an object, the image generating apparatus comprising:
   a memory storing a program; and
   a processor which, by executing the program, functions as:
      an information acquiring unit configured to acquire request information including information representing a requested viewing time of the plurality of images and information representing requested image qualities of the plurality of images;
      a control unit configured to set the image qualities of the plurality of images to the requested image qualities when the plurality of images can be generated with the requested image qualities before the requested viewing time passes, and set the image qualities of the plurality of images to image qualities different from the requested image qualities when the plurality of images cannot be generated with the requested image qualities before the requested viewing time passes; and
      a generating unit configured to generate the plurality of images with the image qualities of the plurality of images set by the control unit.

2. The image generating apparatus according to claim 1, wherein the control unit is configured to decrease the respective image qualities of the plurality of images to a predetermined level when the plurality of images cannot be generated with the requested image qualities before the requested viewing time passes.

3. The image generating apparatus according to claim 1, wherein the information acquiring unit is configured to acquire a specification of respective priorities of the plurality of images as the request information, and
   the control unit is configured to decrease the respective image qualities of the plurality of images in accordance with the priorities of the images when the plurality of images cannot be generated with the requested image qualities before the requested viewing time passes.

4. The image generating apparatus according to claim 1, wherein the information acquiring unit is configured to specify the request information on the basis of a patient category.

5. The image generating apparatus according to claim 4, wherein the control unit is configured to set the image qualities set by the request information to individual images when the patient category includes a secondary test.

6. The image generating apparatus according to claim 4, wherein the information acquiring unit is configured to request a user to input the request information when the patient category includes an emergency patient.

7. The image generating apparatus according to claim 1, wherein the control unit is configured to cause a display unit to display information representing the image qualities of the plurality of images set by the control unit when the plurality of images cannot be generated with the requested image qualities before the requested viewing time passes.

8. An image generating apparatus generating a plurality of images by using a reception signal of an acoustic wave propagated from an object, the image generating apparatus comprising:
   a memory storing a program; and
   a processor which, by executing the program, functions as:
      an information acquiring unit configured to acquire request information including information representing a requested viewing time of the plurality of images and information representing requested image qualities of the plurality of images;
      a control unit configured (a) to set the image qualities of the plurality of images to the requested image qualities when the plurality of images can be generated with the requested image qualities before the requested viewing time passes, or (b) to request a user to input information specifying image qualities different from the requested image qualities when the plurality of images cannot be generated with the requested image qualities before the requested viewing time passes and set the image qualities of the plurality of images specified by the user; and
      a generating unit configured to generate the plurality of images with the image qualities of the plurality of images set by the control unit.

9. A control method for an image generating apparatus generating a plurality of images by using a reception signal of an acoustic wave propagated from an object, the control method comprising:

acquiring request information including information representing a requested viewing time of the plurality of images and information representing requested image qualities of the plurality of images;

setting the image qualities of the plurality of images to the requested image qualities when the plurality of images can be generated with the requested image qualities before the requested viewing time passes;

setting the image qualities of the plurality of images to image qualities different from the requested image qualities when the plurality of images cannot be generated with the requested image qualities before the requested viewing time passes; and generating the plurality of images with the set image qualities of the plurality of images.

10. A control method for an image generating apparatus generating a plurality of images by using a reception signal of an acoustic wave propagated from an object, the control method comprising:

acquiring request information including information representing a requested viewing time of the plurality of images and information representing requested image qualities of the plurality of images;

setting the image qualities of the plurality of images to the requested image qualities when the plurality of images can be generated with the requested image qualities before the requested viewing time passes;

requesting a user to print information specifying image qualities different from the requested image qualities and setting the image qualities of the plurality of images specified by the user when the plurality of images cannot be generated with the requested image qualities before the requested viewing time passes; and generating the plurality of images with the set image qualities of the plurality of images.

\* \* \* \* \*